United States Patent [19]
Tsay et al.

[11] Patent Number: 5,972,632
[45] Date of Patent: Oct. 26, 1999

[54] ANTICOMPLEMENT ACTIVITY ASSAYS

[75] Inventors: Grace C. Tsay, Walnut Creek; Neal Cheung, Vallejo, both of Calif.

[73] Assignee: Bayer Corporation, Berkeley, Calif.

[21] Appl. No.: 07/689,215

[22] Filed: Apr. 22, 1991

[51] Int. Cl.$^6$ .......................... G01N 33/96; A61K 39/395
[52] U.S. Cl. ....................... 435/7.92; 424/177.1; 435/7.5; 435/337; 436/545; 436/804; 436/821; 530/389.3; 530/390.5
[58] Field of Search ...................................... 435/7.92, 7.4, 435/7.5, 337; 436/518, 547, 821, 804, 545

[56] References Cited

PUBLICATIONS

Bing, *Molecular Immunology*, vol.20, No. 8, pp. 893–900, (1983).
Hassig, *Vox Sang.*, vol. 51, pp. 10–17, (1986).
G. Tsay, The FASEB Journal, Abstract 2294, Apr. 26,1990.
A.K. Abbas et al, Cellular and Molecular Immunology, W. B. Saunders Co., Chap. 13, pp. 260–282, 1991.
J.L. Wagner et al, Anal. Biochem. 136, 75–88, 1984.
R.J. Ziccardi et al, Clin. Immunol. and Immuno Path, 15, 465–471, 1980.

*Primary Examiner*—Mary E. Ceperley
*Attorney, Agent, or Firm*—James A. Giblin

[57] ABSTRACT

Immunoassays for complement components, complement activation products or, preferably both, can be used to determine an acceptable level of anticomplement activity (AC) in plasma derived biologically active products intended for infusion into a mammal. In one application an ELISA for complement components (CC) such as C1q, C1r or C1s can be used to determine AC in an IgM-enriched immune serum globulin (ISG). In another application, an immunoassay for complement activation products (CAP) is used for a similar determination. In yet a preferred third application, assays for both a CC (such as measuring a decreasing amount of C1r) and a CAP (such as measuring an increasing amount of C4a) are used to assess the relative AC (and safety) of a biologically active, therapeutic preparation.

2 Claims, 6 Drawing Sheets

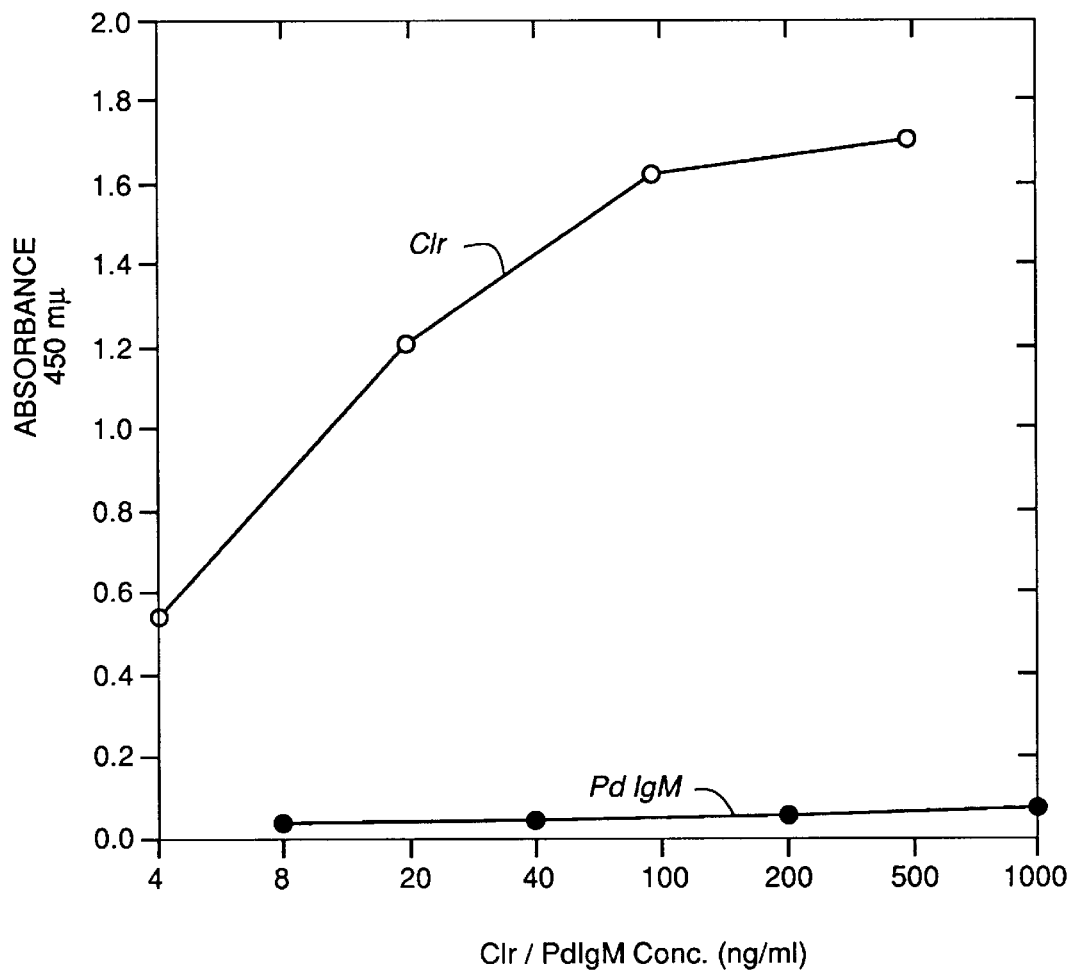
FIG._1A

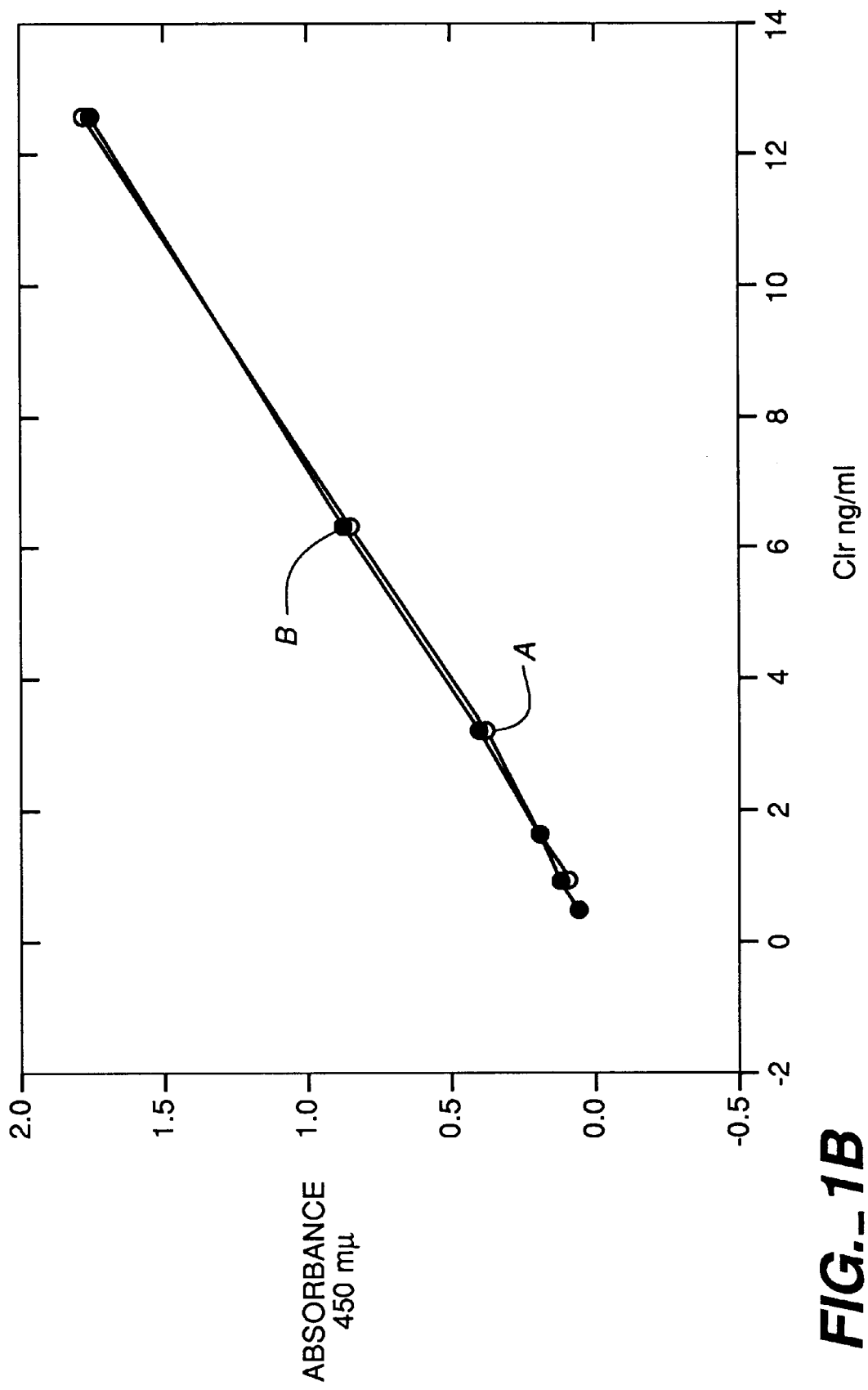
FIG._1B

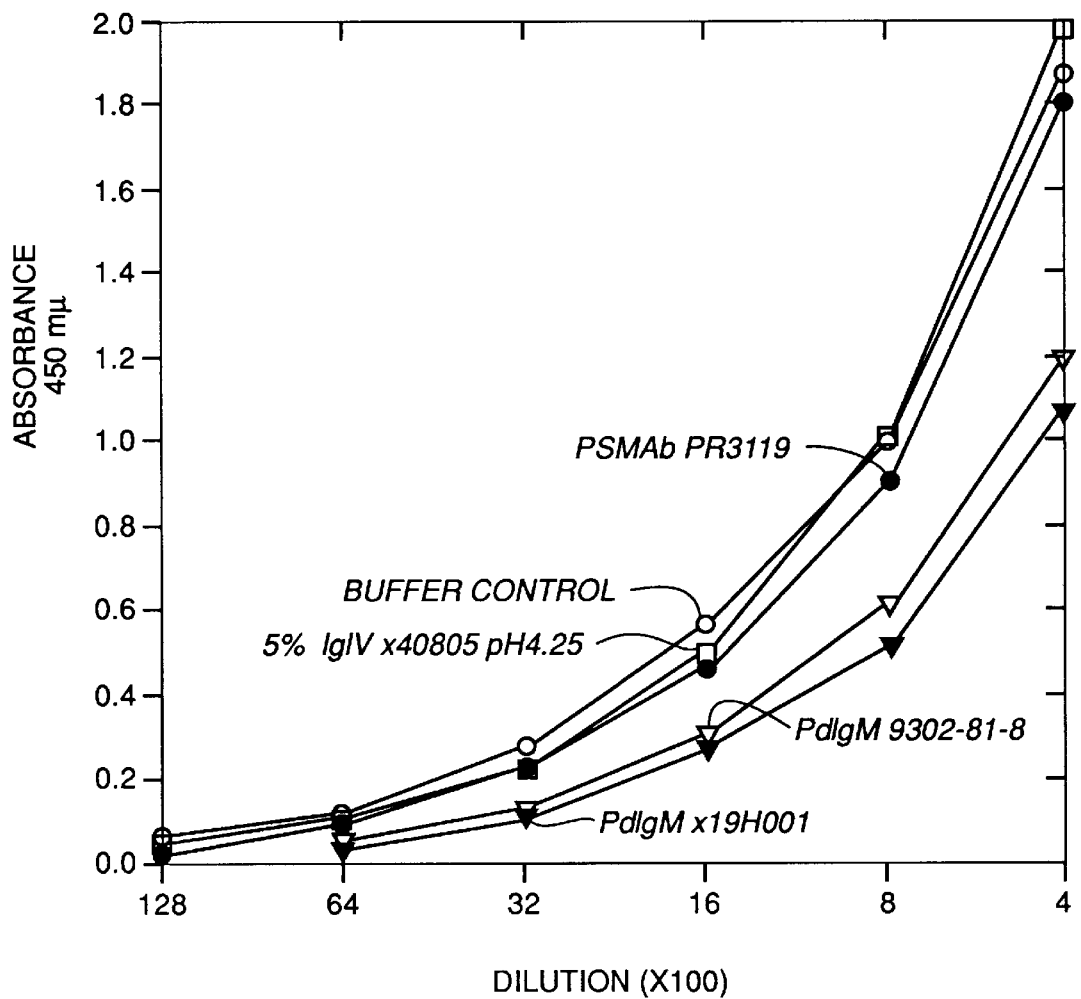
FIG._2

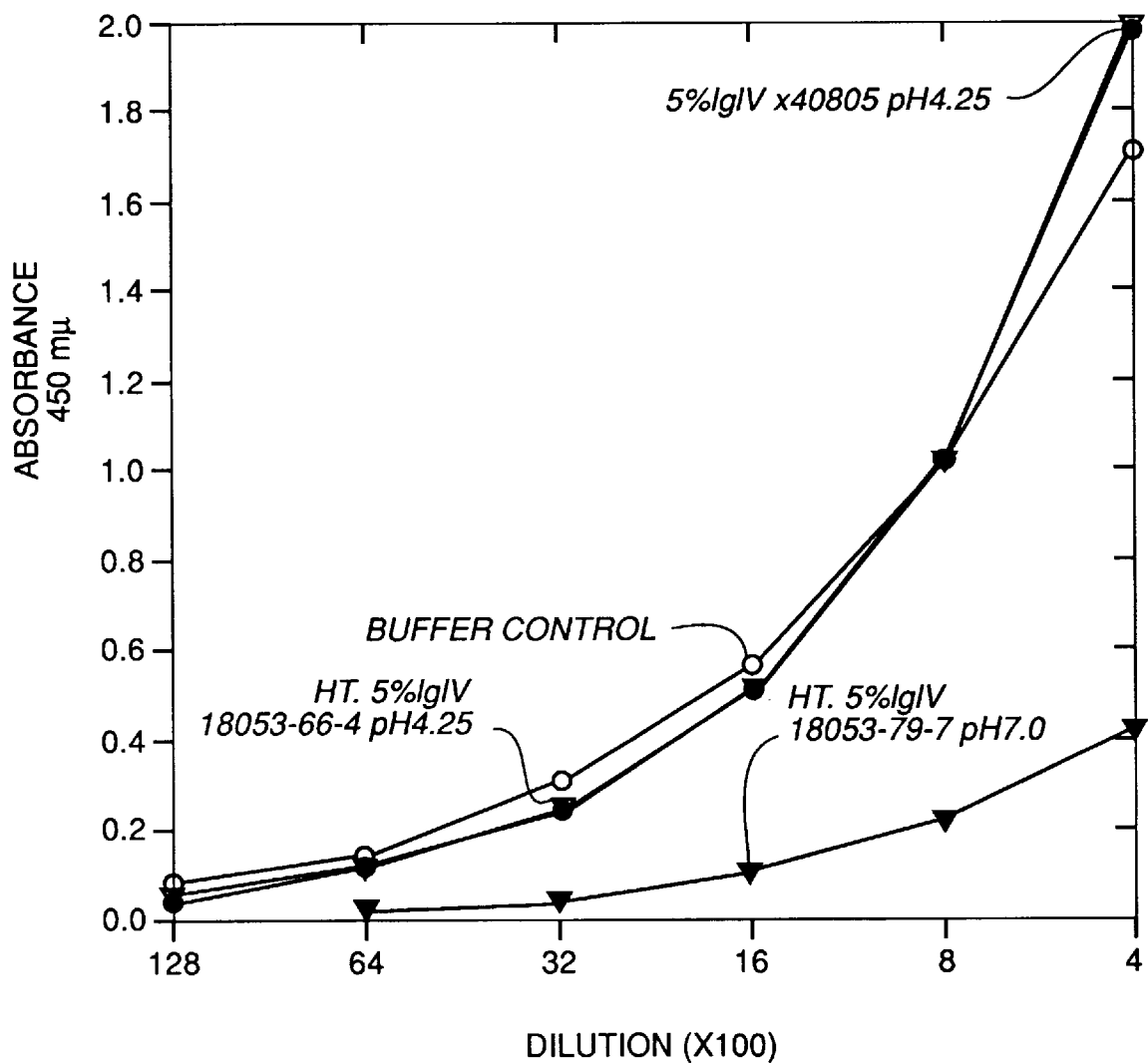
FIG._3

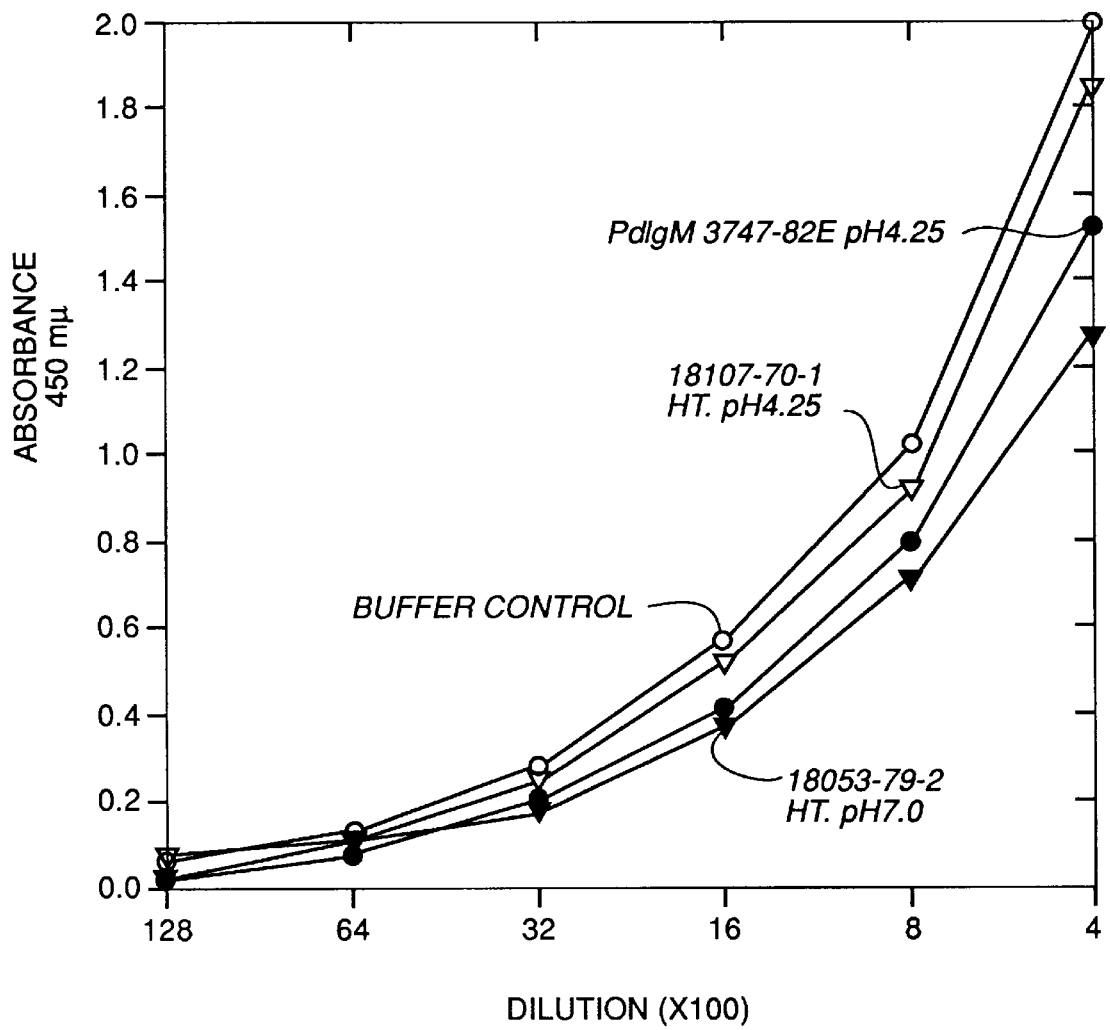
FIG._4

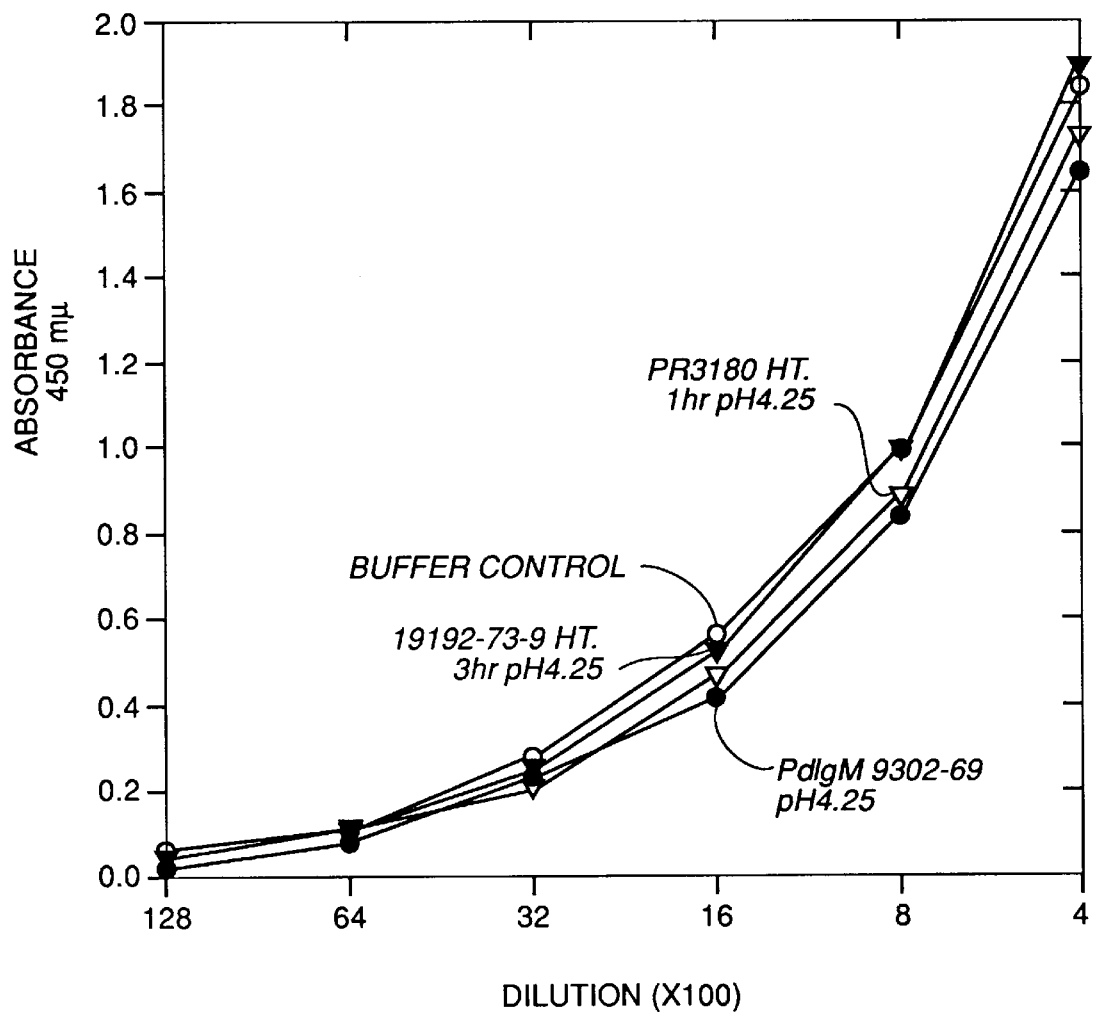
FIG._5

ANTICOMPLEMENT ACTIVITY ASSAYS

BACKGROUND OF THE INVENTION

1. Field

This disclosure is concerned generally with immunoassays and specifically with the use of immunoassays to measure components and products of the complement system of immunology and to use those measurements to determine the relative safety of biologically active products.

2. Prior Art

Immunoassays are assays based on the ability of a given antibody to complex with a very specific substance. Because of the highly specific nature of antibodies to bind with a given substance and the availability of certain "labels" that can be bound to the antibody or the substance, immunoassays can be and are used in very exquisite ways to detect very low concentrations of substances.

Some of the earlier immunoassays used radioactive isotopes as labels. These are referred to as radioimmunoassays or RIA. In another type of immunoassay, the use of isotopes is avoided by using enzymes as labels. The bonded enzymes act on substrates to generate measurable products, thus, indirectly, indicating the amount of substance bearing the enzyme label. A typical immunoassay using an enzyme label is referred to as an ELISA (enzyme linked immunosorbant assay). Since immunoassays usually require a step involving separation of reactants, it is common to immobilize at least one of the reactants on a solid support to facilitate the separation.

The complement system refers to a system of functionally linked proteins that interact with one another in a highly regulated manner to provide, ultimately, what is known generally as an immune response. The system involves what is known as the complement cascades in which various complement components (CC) interact to form various complement activation products (CAP). There are two generally recognized complement cascades, the so-called classical and alternative pathways, both ultimately leading to the formation of a complex known as the membrane attack complex (MAC), also known as C5–9. Complement components, complement activation products and the complement pathways are described in the book by A. K. Abbas et al, Cellular and Molecular Immunology, W. B. Saunders Company, 1991. See especially Chapter Thirteen, The Complement System, pp 260–82, the details of which are incorporated into this disclosure.

While there is much yet to be learned about the complement system, it is known that the complement cascades involve the presence and generation of substances known as complement activation products (such as C4a and C4b), complement complexes (e.g., C5–9) and complement components (e.g., designated C1 through C9, the three subcomponents of C1 being known as C1q, C1r and C1s).

Assays for complement activation products and components have been disclosed by others. See for example, Wagner J L, and Hugli T E, Radioimmunoassay for Anaphylatoxins: A sensitive method for determining complement activation products in biological fluids. Anal Biochem 136:75–88 (1984). Those authors describe utilizing radioimmunoassay (RIA) to determine the complement breakdown products C3a, C4a, and C5a in various clinical materials (e.g. plasma samples) that may prove useful as a diagnostic tool. The assays determined the complement activation of heat-aggregated IgG at neutral pH (7.0).

See also, Tsay GC, and Stambolija L, Heat-aggregated immunoglobulin G induced anaphylatoxin generation (complement activation). Abstract, the FASEB Journal 4:A2089 (1990). This reference describes heat-aggregated IgG prepared at neutral pH (7.0) which induces anaphylatoxin generation (complement activation) in vitro by the RIA method. It was found that aggregates formed at pH 4.25 did not.

Lastly, see Ziccardi R J, and Cooper N R, Development of an immunochemical test to assess C1 inactivator function in human serum and its use for the diagnosis of hereditary angioedema. Clin Immunology and Immunpathol 15:465–471 (1980). This reference describes the diagnosis of C1-inactivator (IN) function in human serum determined with the addition of heat-aggregated IgG at pH 7.0 which activated the C1r and interacted with C1-IN in the sera. This lead to a reduction in the level of antigenically detectable C1r by radial immunodiffusion utilizing mono-specific antiserum to C1r.

We are unaware, however, of the use of immunoassays to determine the anticomplementary activity (and safety) of a biologically active therapeutic product (such as antibody preparations) intended for infusion. Details of such assays are described below.

SUMMARY OF INVENTION

Our immunoassays for complement components, complement activation products or, preferably both, can be used to determine an acceptable level of anticomplement activity (AC) in plasma derived biologically active products intended for infusion into a mammal such as a human. In one application an immunoassay for complement components (CC) such as C1q, C1r or C1s can be used to determine AC in an IgM-enriched immune serum globulin (ISG). In another application, an immunoassay for complement activation products (CAP) is used for a similar determination. In yet a preferred third application, assays for both a CC (such as measuring a decreasing amount of C1r) and a CAP (such as measuring an increasing amount of C4a) are used to assess the relative AC (and safety) of a biologically active, therapeutic preparation.

In preferred embodiments, we employ both a C1r ELISA and a C4a RIA to determine the product safety of immunoglobulin preparations, such as native 5% intravenous immunoglobulin (IgIV), pH 4.25 (Cutter Biological) by incubating it with human serum. We determine whether the potential complement source (the IgIV product being tested) causes non-significant C4a generation (less than about 0.6–1.3 $\mu$g/ml) and non-significant C1r reduction (more than about 52–57.6 $\mu$g/ml) when compared with human serum control. These are the guidelines for the safety significance of measuring AC activity in biological products.

BRIEF DESCRIPTION OF THE FIGURES

FIG. 1a is a graph showing a human C1r standard curve (500 ng/ml to 4 ng/ml) and plasma derived IgM-enriched antibody preparation (1,000 ng IgM/ml to 8 ng IgM/ml) determined by C1r ELISA.

FIG. 1b is a linear graph showing a human C1r standard curve (12 ng/ml to 0.75 ng/ml) by C1r ELISA.

FIGS. 2–4 are graphs showing further ELISAs under different conditions.

FIG. 5 is a graph showing the effect of time on anticomplement activity.

SPECIFIC EMBODIMENTS

As noted above, radioimmunoassay (RIA) of anaphylatoxin generation (C4a) has been reported to detect the anticomplement activity of heat-aggregated immunoglobulin (IgG) at 2 different pH values, 4.25 and 7.0 (See Wagner et al and Tsay et al, cited above). C1-inactivator (IN) function in human serum was determined with the addition of complement activator, heat-aggregated IgG (pH 7.0) that activated the C1r and interacted with C1-IN in the sera leading to a reduction in the levels of antigenically detectable C1r by radial immunodiffusion utilizing mono-specific antiserum to C1r (see Ziccardi et al, cited above). We have found that similar principles can be applied to detect anticomplement activity of immunoglobulin preparations by utilizing normal human serum as source containing C1-IN, C1r, and by determining C1r concentration by enzyme-linked immunosorbent assay (ELISA).

This disclosure describes the anticomplement activity of immunoglobulin preparations such as IgM, IgG immunoglobulin concentrates, purified IgG at 2 different pH 4.25, 7.0, and heat treatment of IgG or IgM concentrates being assessed by C1r ELISA and by comparison with C4a RIA.

MATERIALS AND METHODS

Cohn Fraction III paste prepared as a by-product from pooled normal plasma following methods of Cohn et al (J. Am. Chem. Soc. 68:459–75, 1946) and Oncley et al (J. Am Chem Soc 71:541–550, 1949) at Cutter Biological, Miles Inc. served as the source material for plasma-derived (pd) IgM, IgG immunoglobulin concentrates preparation. 5% IGIV (X40B05) was prepared by Cutter Biological, Miles Inc. from Cohn Fraction II effluent in 10% maltose pH 4.25.

Pd IgM, IgG Immunoglobulin Concentrates Preparation

Plasma-derived (pd) IgM immunoglobulin concentrates were isolated from Cohn Fraction III paste, suspended in 12.5 volumes of 0.05 M acetate buffer pH 3.5–4.0, and mixed at room temperature for 2–3 hours. To the mixture was added 1–2.0% caprylic acid and by vol/wt at pH 4.8 to remove lipoproteins and prekallikrein activator (PKA) by centrifugation. The extracted caprylate supernatant, after diafiltration and ultrafiltration through PM-30, resulted in low conductivity of 0.03–0.06 mmho/cm at pH 4.8. Virus inactivation was achieved with 0.3% TNBP/1% Tween-80 detergent at 24° C. for more than 6 hours. The caprylate supernatant was precipitated with buffer system such as Tris (0.0101 vol. of 1 M tris pH 7.8) or imidazole buffer (0.005 vol. of 1 M imidazole pH 7.8). The precipitant was further dissolved in sterile water, adjusting pH to 4.0–4.25 with acetic acid and further diafiltered/ultrafiltered against water, then adding solid glycine to a final concentration of 0.25 M glycine pH 4.25 or solid maltose to a final concentration of 10% maltose pH 4.25. The final IgM concentrates consisted of 50–60% IgM, 30–40% IgG, 5–10% IgA in a total 5% protein aqueous solution.

Heat-agaregated IgG Preparation

A 5% solution of IGIV (X40B05) was used as an appropriate antibody control. A heat-aggregated IgG solution was prepared from the 5% IGIV solution by heating at 63° C. for 1 hour (pH 7.0). Another heat-aggregated IgG solution was prepared from the 5% IGIV solution by heating at 62° C. for 2 hours (pH 4.25).

Heat-treated IaM, IgG Immunoalobulin Concentrates Preparation

The heat treatment of the IgM, IgG immunoglobulin concentrates preparation in glycine or maltose pH 4.25 or pH 7.0 ranged from 50° C. to 62° C. for 1 to 3 hours.

Aggregate Determination by HPLC

Aggregate formation in the native IgM and IgG preparations or induced by heating was determined by high pressure liquid chromatography (HPLC) with TSK G4000 SWXL gel for IgM or TSK G3000 SWXL (7.8×300 mm, 8 $\mu$m particle size, Toyo Soda Corporation, Japan) for IgG and eluted with 0.05 M sodium acetate, 0.20 M sodium sulfate pH 5.0.

Determination of IaM, IaG Concentration by RID/Nephelometry Assay (NPA)

The concentration of IgM, IgG was determined by radial immuno-diffusion with quiplate system from Helena Laboratories (Beaumont, Tex.) or measured as antigenic protein by using Behring Nephelometer (Behring Diagnostics, San Diego, Calif.) to quantitatively determine the generation of light scattering immune complexes between IgM, IgG, and polyclonal antihuman IgM, IgG by nephelometry with infrared light from a light emitting diode.

C1r Determination by ELISA i. Preparation of Biotin-labeled goat antisera to human C1r. Two ml of goat antisera to human C1r (6.8 mg/mL, Atlantic Antibodies, ATAB) was dialyzed against 4 L of PBS overnight. The dialyzed goat antisera to human C1r were mixed with 0.4 ml of 0.2 M $NaHCO_3$ in 0.15 M KCl pH 8.8 and 50 $\mu$l of biotinyl-N-hydroxy-succinimide ester (6 mg/mL) in dimethylformamide. The mixtures were rotated for 30 minutes at room temperature. The reaction was stopped by adding 100 $\mu$l of 1 M $NH_4Cl$ (pH 6.0). The biotin-labeled goat antisera to C1r were dialyzed against 4 L of PBS with at least 2 times buffer change.

ii. In vitro activation of immunoglobulin preparations with human serum. The immunoglobulin preparations (2.4 mg IgM or IgG/mL serum) was incubated with human serum at 37° C. for 30 minutes and determined the C1r levels by enzyme-linked immunosorbent assay (ELISA).

iii. ELISA. Nunc immunoplates were coated with 0.1 mL of goat antisera to C1r diluted 1:1700 (4 $\mu$g/mL) in bicarbonate buffer pH 9.6 and incubated overnight at 5° C. The plates were washed in PBS with 0.05% Tween-20. After washing, standard HC1r (Calbiochem, San Diego, Calif.), human serum activated with immunoglobulin preparations or human serum control being 2-fold serial diluted in 0.5 M NaCl, 0.5% Tween-20 pH 8.0 were applied to the plates and incubated at 37° C. for 90 minutes. Control wells contained 0.1 mL of dilution buffer 0.5 M NaCl, 0.5% Tween-20 pH 8.0. After washing, biotinylated goat antisera to C1r (1:1000) diluted in 0.5% casein containing 0.15 M NaCl, 0.01 M Tris pH 7.6 buffer were added to the plates and incubated at 37° C. for 90 minutes. After washing, peroxidase conjugated strepavidin (1:5000) diluted in PBS-1% BSA was applied to the plates and incubated at 37° C. for 45 minutes. After the final wash, the substrate solution (tetramethyl benzidine) was added to the reaction was stopped with 6 N $H_2SO_4$. The absorbance of each well was read at 450 nm.

Complement Activation Assessed by Anaphylatoxin (C4a) Generation

The ability of various immunoglobulin preparations to activate the classical pathway of complement in vitro was assessed by incubation of the respective preparations (1.47 mg IgM or IgG/mL serum) with human serum at 37° C. for 20 minutes and determining the resultant generation of C4a levels by radioimmunoassay (RIA). The RIA kits were obtained from Amersham (Arlington Heights, Ill.).

RESULTS

In order to determine AC activity of immunoglobulin preparations by measuring a decreasing amount of C1r, the C1r ELISA assay was introduced. The concentrations of C1r in human serum were determined by C1r ELISA with the optimal condition of monospecific antiserum to human C1r coated to the plates (4 µg/ml). FIG. 1a and 1b show the purified human C1r standard can be detected, the concentration range (0.75–12 ng/ml) by C1r ELISA and goat antiserum to C1r is specifically reacted to C1r but does not cross react to IgM, IgG immunoglobulin concentrates.

The following examples were carried out to show that the reduction of C1r concentration measured during activation of C1r on human serum by known complement activators. This was correlated with C4a generation determined by C4a RIA.

EXAMPLE 1

Human serum in the absence of complement activator contained about 54–60.8 µg/mL of HC1r determined from standard curve of C1r ELISA (FIG. 1b, Table 1). Human serum in the presence of complement activator such as IgM, IgG immunoglobulin concentrates Preparation No. (9302-81-8, Preparation No. X19H001) prepared from Cohn Fraction III paste in 0.25 M glycine or 10% maltose pH 4.25 resulted in C1r reduction to 33–38 µg/mL, about 37% reduction compared to the human serum control (FIG. 2). However, human serum in the presence of Ps MAb PR 3119, 5% IGIV X40B05 pH 4.25 resulted in non-significant C1r reduction (50–57 µg/mL, FIG. 2). These results indicate that IgM, IgG immunoglobulin concentrates contain high anticomplement (AC) activity monitored by C1r reduction and 5% IGIV, Ps MAb contains low (non-significant) AC activity.

EXAMPLE 2

5% IGIV in 10% maltose pH 4.25 or pH 7.0 heated at 63° C. for 1 to 2 hours generated 59% aggregate (molecular size=≦pentamer) at pH 4.25 but generated 5% aggregate (molecular size=>pentamer) at pH 7.0. Heat-aggregated IgG at pH 4.25 incubated with human serum resulted in non-significant C1r reduction (53.6 µg/mL) and non-significant C4a generation (0.86 µg/mL) (FIG. 3, Table 1). However, heat-aggregated IgG at pH 7.0 incubated with human serum resulted in C1r reduction (6.8–8.8 µg/mL) and C4a generation (13.5–21.5 µg/mL, FIG. 3, Table 1). The heat-aggregated IgG at pH 7.0, but not at pH 4.25, caused complement activation that correlated with C1r reduction and C4a generation on activated human serum.

TABLE 1 pH Effect for Anticomplement Activity of Heat-aggregated Immunoglobulin G by HC1r ELISA and C4a RIA

| IgG Preparation | Heat 63° C. Min. | mg/mL RID | IgG % Aggregate (>) | IgG % Aggregate (≦) Pentamer | HC1r µ/mL | C4a µ/mL |
|---|---|---|---|---|---|---|
| 5% IGIV in 10% Maltose Preparation NO. (X40B05) | | | | | | |
| pH 4.25 | 0 | 48.86 | 0 | 0 | 57.6 | 0.51–0.80 |
| pH 4.25 | 120 | 21.11 | 0 | 58.8 | 53.6 | 0.86 |
| pH 7.0 | 0 | 49.31 | 0 | 3.0 | 56.0 | 1.83 |
| pH 7.0 | 60 | 42.07 | 5.0 | 16.0 | 6.8–8.8 | 13.5–21.5 |
| H. Serum Control | — | — | — | — | 54–58.6 | 0.40 |

EXAMPLE 3

Plasma-derived IgM, IgG immunoglobulin concentrates, Preparation No. (18189-1-I, Preparation No. 3747-82-E) in 0.25 M glycine pH 4.25 heated at 50° C. for 3 hours resulted in 7–10% aggregates and decreased non-specific complement activation by C1r increased from 38 µg/mL to 55–58 µg/mL and C4a decrease from 8.9 µg/mL to 0.9 µg/mL (FIG. 4, Table 2). However, pd IgM concentrates (3747-82-E) at pH 7.0 heated at 62° C. for 1 hour resulted in 17% aggregate and increased anticomplement activity by C1r reduction from 38 µg/mL to 35 µg/mL and C4a generation from 8.9 µg/mL to 16.8 µg/mL (FIG. 4, Table 2). Plasma-derived IgM concentrates (9302-69) in 10% maltose pH 4.25 heated at 50° C. for 1 hour resulted in 16.5% aggregate formation, C1r increase from 40 µg/mL to 44 µg/mL, and C4a reduction from 7.7 µg/mL to 3.4 µg/mL when incubated with human serum. But pd IgM concentrates (9302-69) heated for 2–3 hours resulted in less C1r reduction (48 to 54 µg/mL) and less C4a generation (1.8 to 1.5 µg/mL) (FIG. 5, Table 3). The similar results (in Table 3) indicate that pd IgM concentrate (19180-45-1) in 10% maltose pH 4.25 heated at 50° C. for 1, 2, and 3 hours resulted in less C1r reduction for 3 hours (52 µg/mL), then 1 hour (47.5 µg/mL) and no significant C4a reduction for 3 hours and 1 hour, both being 2.4–2.0 µg/mL. These results demonstrate that pd IgM concentrates heated at pH 4.25 for 3 hours resulted in less anticomplement activity than unheated pd IgM concentration and correlated well by both C1r and C4a generation when incubated with human serum.

TABLE 2 pH Effect for Anticomplement Activity of Heat-treated IgM Concentrates by C1r ELISA and C4a RIA

| | IgM/IgG Immunoglobulin Concentrates | HT °C. | Hr | IgM mg/mL | IgG mg/mL | % Aggregate | Hc1r µg/mL | C4a µg/mL |
|---|---|---|---|---|---|---|---|---|
| 1. | 18189-1-I | | | | | | | |
| | pH 4.25 | 5 | — | 31 | 22.5 | ND | 38.5 | 8.1 |
| | pH 4.25 | 52 | 3 | 24 | 20.5 | 7.0 | 54.6 | 0.9 |
| 2. | 3747-82-E | | | | | | | |
| | pH 4.25 | 5 | — | 35.4 | 24.3 | 4.0 | 38.0 | 8.9 |
| | pH 4.25 | 50 | 3 | 32.9 | 24.4 | 10.0 | 58.8 | 0.9 |
| | pH 7.0 | 5 | — | 36.0 | 24.3 | 12.0 | 40.0 | 12.2 |
| | pH 7.0 | 62 | 1 | 8.0 | 11.5 | 17.0 | 34.8 | 16.8 |
| 3. | H. Serum Control | — | — | — | — | — | 54–60.8 | 0.4 |

TABLE 3

Time Effect for Anticomplement Activity of Heat-treated IgM Concentrates by Human C1r ELISA and C4a RIA

| | IgM/IgG Immunoglobulin Concentrates | HT °C. | Hr | IgM mg/mL | IgG mg/mL | % Aggregate | Hc1r µg/mL | C4a µg/mL |
|---|---|---|---|---|---|---|---|---|
| 1. | 19180-45-1 | 5 | — | 41.4 | 10.1 | 10.1 | 40.4 | 13.4 |
| | | 50 | 1 | 47.8 | 10.9 | 11.8 | 47.6 | 2.0 |
| | | 50 | 2 | 45.1 | 10.1 | 15.9 | 48.8 | — |
| | | 50 | 3 | 45.1 | 10.4 | 18.0 | 52.0 | 2.4 |
| 2. | 9302-69 | 5 | — | 24.7 | 27.6 | 6.4 | 40.4 | 7.7 |
| | | 50 | 1 | 30.3 | 30.8 | 16.5 | 44 | 3.4 |
| | | 50 | 2 | 33.1 | 30.7 | 17.4 | 48.4 | 1.8 |
| | | 50 | 3 | 31.8 | 30.7 | 18.8 | 53.6 | 1.5 |
| 3. | Control HT IgG (pH 7.0) | 62 | 1 | — | — | 21.0 | 6.8–8.8 | 13.5–21 |
| | 5% IGIV (pH 4.25) | 5 | — | — | — | 0 | 52–57.6 | 0.6–1.3 |
| | 10% Maltose Control | — | — | — | — | — | 54–58.6 | 0.40 |

DISCUSSION AND CONCLUSION

Determination of C4a generation in vitro incubated with human serum as complement source (see Tsay et al, FASEB Journal 4:A2089,1990) is correlated to the adverse effects of infused heat aggregated IgG in vitro (see Bleeker et al, Vox Sang 52:281-90, 1987 and Jesmok et al, Circ Shock 31:9–10, 1990). The development of a C1r ELISA to determine C1r concentration on human serum incubated with complement activator is a marker to monitor complement activation. Human serum as a complement source should contain C1 inactivator function in order to interact with C1r activated with complement activator (see Ziccardiet et al, Clin Immunol Immunopath 15:465–471,1980). Heat-aggregated IgG at pH 7.0 and pd IgM, IgG immunoglobulin concentrates when incubated with human serum caused C1r reduction about 86% of human serum control for heat-aggregated IgG (pH 7.0) and 30–52% C1r reduction for pd IgM, IgG immunoglobulin concentrates. These results show that heat-aggregated IgG (pH 7.0) and pd IgM, IgG concentrates (complement activator) activated C1r binding to C1-inactivator with resulting loss of C1r antigenicity and caused C1r reduction when incubated with human serum.

The reduction of clr concentration and increase in C4a generation for the heat-aggregated IgG (pH 7.0) and pd IgM, IgG immunoglobulin concentrates which incubated with human serum served as indicators for the complement activation of this immunoglobulin preparation. However, heat-aggregated IgG at pH 4.25, native IGIV pH 4.25 and heat-treated pd IgM, IgG immunoglobulin concentrates at pH 4.25 for 3 hours resulted in non-significant C1r reduction and non-significant C4a generation when incubated with human serum.

These results also indicate that native IGIV, heat-aggregated IgG (pH 4.25) and heat-treated pd IgM concentrates (pH 4.25) cause non-significant complement activation by C1r ELISA and c4a RIA. Heat treatment of pd IgM concentrate at pH 7.0 resulted in C1r reduction (38% of human serum control) and C4a generation (16.8 $\mu$g/mL) when incubated with human serum. These data suggest that heat treatment of IgG or pd IgM concentrates at pH 7.0 cause significant non-specific complement activation when incubated with human serum. But heat treatment at pH 4.25 resulted in non-significant complement activation determined by C1r ELISA and C4a RIA. Therefore, C1r determination by C1r ELISA and C4a generation by RIA may provide the analysis tools for anticomplement activity determination of various immunoglobulin preparations.

Given the above disclosure, it is thought that variations will occur to those skilled in this field. Accordingly, it is intended that the scope of the invention disclosed here should be limited only by the following claims.

We claim:

1. A method of determining the anticomplement activity of an immunoglobulin biological product intended for infusion, the method comprising the steps of
    (A) contacting the product with human serum and then separately contacting the human serum with immobilized antibody preparations that specifically bind to complement component C1r and complement activation product C4a in the serum;
    (B) separately measuring the amounts of the C1r and C4a that bind to the respective antibody preparations;
    (C) comparing the amounts of the C1r and the C4a bound to the respective antibody preparations with standards to determine the amounts of C1r and C4a in the serum; and
    (D) using the determinations of step (C) to determine the anticomplement activity of the product.
2. The method of claim 1 wherein the immunoglobulin product is an antibody preparation having a pH of about 4.25.

* * * * *